(12) United States Patent
Carvalho et al.

(10) Patent No.: US 7,195,774 B2
(45) Date of Patent: Mar. 27, 2007

(54) IMPLANTABLE AND SEALABLE SYSTEM FOR UNIDIRECTIONAL DELIVERY OF THERAPEUTIC AGENTS TO TISSUES

(76) Inventors: Ricardo Azevedo Pontes de Carvalho, 600 N. Wolfe St—Maumenee Building Suite 517, Baltimore, MD (US) 21287; Alan Linn Murphree, 80 N. Euclid Ave. #302, Pasadena, CA (US) 91101; Edward E. Schmitt, 2344 Colombia St., Palo Alto, CA (US) 94306

( * ) Notice: Subject to any disclaimer, the term of this patent is extended or adjusted under 35 U.S.C. 154(b) by 470 days.

(21) Appl. No.: 10/231,767

(22) Filed: Aug. 28, 2002

(65) Prior Publication Data

US 2003/0064088 A1 Apr. 3, 2003

Related U.S. Application Data

(60) Provisional application No. 60/315,952, filed on Aug. 29, 2001.

(51) Int. Cl.
*A61F 2/00* (2006.01)
(52) U.S. Cl. .................................. 424/427
(58) Field of Classification Search ............... 424/423, 424/130.1, 427–29; 623/4.1, 5.11, 5.13; 604/890.1
See application file for complete search history.

(56) References Cited

U.S. PATENT DOCUMENTS

| | | | |
|---|---|---|---|
| 4,309,776 A | | 1/1982 | Berguer |
| 4,378,016 A | | 3/1983 | Loeb |
| 4,479,796 A | | 10/1984 | Kallok |
| 4,549,529 A | * | 10/1985 | White ..................... 128/898 |
| 4,768,523 A | * | 9/1988 | Cahalan et al. .......... 607/116 |
| 4,978,338 A | * | 12/1990 | Melsky et al. ......... 604/288.02 |
| 5,182,111 A | | 1/1993 | Aebischer et al. |
| 5,292,362 A | * | 3/1994 | Bass et al. ............. 106/173.01 |
| 5,411,550 A | | 5/1995 | Herweck et al. |
| 5,443,505 A | * | 8/1995 | Wong et al. ................. 623/4.1 |
| 5,445,616 A | * | 8/1995 | Kratoska et al. ............ 604/141 |
| 5,558,630 A | * | 9/1996 | Fisher ......................... 604/8 |
| 5,725,493 A | | 3/1998 | Avery et al. |
| 5,773,019 A | * | 6/1998 | Ashton et al. ............. 424/423 |
| 5,830,173 A | | 11/1998 | Avery et al. |
| 5,836,935 A | | 11/1998 | Ashton et al. |
| 5,902,598 A | | 5/1999 | Chen et al. |
| 6,001,386 A | | 12/1999 | Ashton et al. |
| 6,217,895 B1 | | 4/2001 | Guo et al. |

(Continued)

OTHER PUBLICATIONS

Ratner et al., Biomaterials Science: An Introduction to Materials in Medicine, 1996, Academic Press, pp. 322-323.*

(Continued)

*Primary Examiner*—Sharon E. Kennedy
(74) *Attorney, Agent, or Firm*—Daniel B. Schein, Esq.

(57) ABSTRACT

A surgically implantable and sealable delivery device that upon contact of its contents via an interface window or port therein with an organ or tissue exposes a therapeutic agent to the organ or tissue surface, allowing a controlled, selective and unidirectional diffusion of the agent into the tissue or organ. The device protects adjacent organs or tissue structures from unnecessary high levels of the delivered agent. Novel methods to deliver chemotherapeutics or bioactive agents to mammalian organs or tissues through a surgically implanted device by the way of a selective and protected diffusion mechanism are disclosed as well as method to achieve the sealing properties of the device.

72 Claims, 6 Drawing Sheets

U.S. PATENT DOCUMENTS

| | | |
|---|---|---|
| 6,251,090 B1 | 6/2001 | Avery et al. |
| 6,413,540 B1 | 7/2002 | Yaacobi |
| 6,416,777 B1 | 7/2002 | Yaacobi |
| 6,726,920 B1 * | 4/2004 | Theeuwes et al. ......... 424/423 |
| 7,008,396 B1 * | 3/2006 | Straub ........................ 604/8 |
| 2002/0188282 A1 * | 12/2002 | Greenberg ............. 604/890.1 |
| 2003/0064088 A1 | 4/2003 | Carvalho et al. |
| 2003/0069560 A1 | 4/2003 | Adamis et al. |
| 2004/0024453 A1 * | 2/2004 | Castillejos ................. 623/4.1 |
| 2004/0106906 A1 * | 6/2004 | Yaacobi ..................... 604/294 |

OTHER PUBLICATIONS

U.S. Appl. No. 60/334,177, filed Nov. 29, 2001, Borenstein et al.
U.S. Appl. No. 60/332,200, field Nov. 21, 2001, Borenstein et al.
U.S. Appl. No. 60/332,199, filed Nov. 21, 2001, Borenstein et al.
U.S. Appl. No. 60/291,445, filed May 16, 2001, Borenstein et al.
U.S. Appl. No. 60/291,340, filed May 16, 2001, Borenstein et al.
U.S. Appl. No. 60/288,373, filed May 3, 2001, Borenstein et al.
Torres-Lugo, Madeline., et al., "Transmucosal delivery systems for calcitonin: a review", *Biomaterials*, vol. 21, pp. 1191-1196 (2000).
Benes, L., et al., "Transmucosal, Oral Controlled-Release, and Transdermal Drug Adminstration in Human Subjects: A Crossover Study with Melatonin", *Journal of Pharmaceutical Sciences*, vol. 86, No. 10, pp. 1115-1119 (1997).
Gebhardt, Bryan M., et al., "Collagen as a Delivery System for Hydrophobic Durg: Studies with Cyclosporine", *Journal of Ocular Pharmacology and Therapeutics*, vol. 11, No. 3, pp. 319-327 (1995).
Kanpolat, Ayfer., et al., "Penetration of Cyclosporin A into the Rabbit Cornea and Aqueous Humor after Topical Drop and Collagen Shield Adminstration", *The CLAO Journal*, vol. 20, No. 2, pp. 119-122 (1994).
Lehr, C-M., "From sticky stuff to sweet receptors—Achievements, limits and novel approaches to bioadhsion", *European Journal of Drug Metabolism and Pharmacokinetics*, vol. 21, No. 2, pp. 139-148 (1996).
Rudnick, David E., et al., "The effect of Intraocular Pressure on Human and Rabbit Scleral Permeability", *IOVS*, vol. 40, No. 12, pp. 3054-3058 (1999).
Olsen, Timothy W., et al., "Human Sclera: Thickness and Surface Area", *American Journal of Ophthalmology*, vol. 125, No. 2, pp. 237-241 (1998).
Olsen, Timothy W., et al., "Human Scleral Permeability", *Investigative Ophthalmology & Visual Science*, vol. 36, No. 9, pp. 1893-1903 (1995).
Brem, Henry., et al., "Placebo-controlled trial of safety and efficacy of intraoperative controlled delivery by biodegradable polymers of chemotherapy for recurrent gliomas", *The Lancet*, vol. 345, pp. 1008-1012 (1995).
Valtonen, Simo., et al., Interstitial Chemotherapy with Carmustine-loaded Polymers for High-grade Gliomas: A Randomized Double-blind Study Clinical Study, *Neurosurgery*, vol. 41, No. 1, pp. 44-49 (1997).
Subach, Brian R., et al., "Morbidity and Survival after 1.3-*bis*(-chloroethyl)-1-Nitrosourea Wafer Implantation for Recurrent Glioblastoma: A Retrospective Case-matched cohort series", *Neurosurgery*, vol. 45, No. 1, pp. 17-23 (1999).
Moriya, T., et al., "Controlling Malignant Pericardial Effusion by Intrapericardial carboplatin Adminstration in Patients with Primary Non-Small-Cell Lung Cancer", *British Journal of Cancer*, vol. 83, No. 7, pp. 858-862 (2000).
Lerner-Tung, Mary B., et al., "Pharmacokinetics of intrapericardial adminstration of 5-fluorouracil", *Cancer Chemother Pharmacol*, vol. 40, pp. 318-320 (1997).
Darsinos, J. TH., et al., "Distribution of lidocaine and digoxin in heart tissues and aorta following intrapericardial adminstration", *International Journal of Clinical Pharmacology, Therapy and Toxicology*, vol. 31, No. 12, pp. 611-615 (1993).
Darsinos, J. T., et al., "Distribution of amiodarone in heart tissues following intrapericardial adminstration", *International Journal of Clinical Pharmacology and Therapeutics*, vol. 37, No. 6, pp. 301-306 (1999).
Uchida, Y., et al., "Angiogenic therapy of acute myocardial infarction by intrapeicardial injection of basic fibroblast growth factor and heparin sulfate: An experimental study", *American Heart Journal*, vol. 36, No. 6, pp. 1182-1188 (1995).
Laham, Roger J., "Intrapericardial Administration of Basic Fibroblast Growth Factor; Myocardial and Tissue Distribution and Comparison With Intracoronary and Intravenous Administration", *Catheterization and Cardiovascular Interventions*, vol. 58, pp. 375-381 (2003).
D'Hermies, Francois., et al., "Scleral and episcleral histological changes related to encircling explants in 20 eyes", *ACTA Ophthalmologica Scandinavica*, vol. 77, pp. 279-285 (1999).
D'Hermies, Francois., et al., "Encapsulation of Scleral Buckling Materials", *Ophthamology*, vol. 105, No. 6. (1998).
Ricci, Benedetto., et al., "Octyl 2-cyanoacrylate tissue adhesive in experimental scleral buckling", *Acta Ophthalmol. Scand.*, vol. 78, pp. 506-508 (2001).
Korobelnik, J. F., "Expanded Polytetrafluoroethylene Episcleral Implants Used as Encircling Scleral Buckling", *Opthalmic Res*, vol. 32, pp. 110-117 (2000).
Mulvihill, Alan., et al. "Ocular Motility Changes After Subtenon Carboplatin Chemotherapy for Retinoblastoma", *Arch Ophthalmo.* vol. 121, pp. 1120-1124 (2003).
D'Hermies, F., "Alterations Anatomopathologiques Liees Au Traitement Par Cerclage Des Golbes Oculaires Atteints De Decollement De Retine", *Sociate D'ecition de l'Association de'Enseignement Medical des Hopitaux de Paris.* pp. 215-222 (1999).
Korobelnik, J. F. et al., "e-PTFE as Scleral Buckling Episcleral Implants: An Experimental and Histopathologic Study", *John Wiley & Sons, Inc. J Biomed Mater Res* vol. 48, pp. 807-813 (1999).
D'Hermies, F. et al., "Experimental Encircling Scleral Buckle With Silicone and Hydrogel", *The Journal of Retinal and Vitreous Diseases.* vol. 19 No. 2, pp. 148-157.
D'Hermies, F. et al., "Miragel Versus Silastic Used As Episcleral Implants in Rabbits", *Retina* vol. 15 No. 1 pp. 62-67 (1995).
Spitznas, M. et al., "Retinal Surgery Using Cyanoacrylate as a Routine Procedure", *Arch. Klin. exp. Ophtal.* vol. 187, pp. 89-101 (1973).
Calabria, G. et al., "Sutureless Scleral Buckling", *Arch Ophtal.* vol. 83, pp. 613-618 (1970).
Calabria, G. et al., "Further Experience With Sutureless Scleral Buckling Materials", *Arch Ophthal.* vol. 86, pp. 82-87 (1971).
Olsen, T.W. et al., "An Evaluation of an Episcleral Anecortave Acetate Transscleral Drug Delivery System in Rhesus Monkey", *Invest Ophthalmol Vis Sci.* vol. 44, p. 4213 (2003).
Yaacobi, Y. et al., "In-Vivo Studies with Trans-Scleral Anecortave Acetate Delivery Device Designed to Treat Choroidal Neovscularization in AMD", *Invest Ophthalmol Vis Sci.* vol. 44, p. 4210 (2003).
Olsen, T. et al., "Human Sclera: Thickness and Surface Area", *American Journal of Ophthalmology.* vol. 125. No. 2, pp. 237-241 (1998).
Harbour, J. et al., "Transducible Peptide Therapy for Uveal Melanoma and Retinoblastoma", *Arch Ophthalmol.* vol. 120, pp. 1341-1346 (2002).
Sayani, A. et al., "Systemic Delivery of Peptides and Proteins Across Absorptive Mucosae", *Therapeutic Reviews™ in Therapeutic Drug Carrier Systems.* 13(1&2): 84-185 (1996).

\* cited by examiner

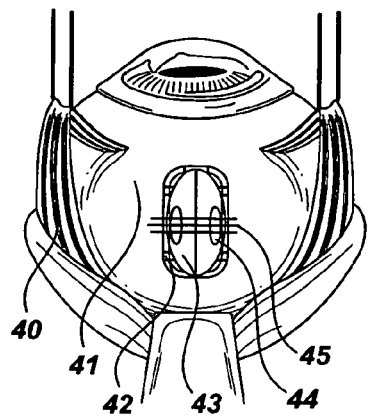
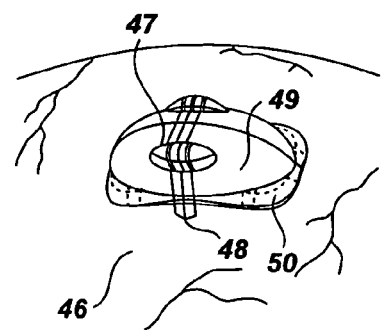
Fig. 8  Fig. 9
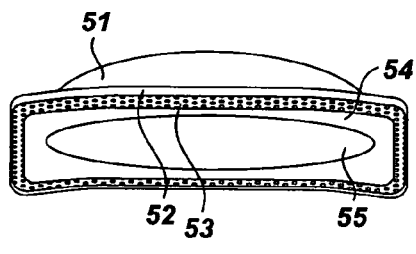
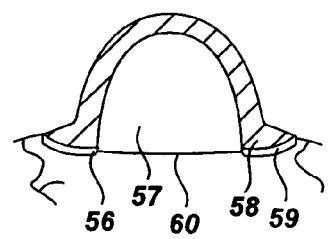
Fig. 10  Fig. 11
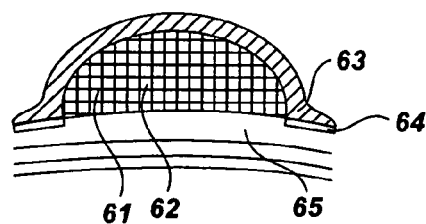
Fig. 12

IMPLANTABLE AND SEALABLE SYSTEM FOR UNIDIRECTIONAL DELIVERY OF THERAPEUTIC AGENTS TO TISSUES

PRIORITY DATA

This application claims priority of U.S. provisional application Ser. No. 60/315,952, filed Aug. 29, 2001.

FIELD OF THE INVENTION

This invention relates to devices and methods for local drug delivery, and in particular is directed to an implantable system that once is hermetically sealed to an organ or tissue protects a therapeutic agent intended for delivery to a target tissue from exposure to surrounding tissues and fluids while still achieving sustained levels, regionally or systemically, in a mammalian organism, methods for implanting same, and methods and devices for treating diseases.

BACKGROUND OF THE INVENTION

The development of drug delivery devices for implantation into a pre-selected locus in mammals has been extensively studied. To date, a variety of surgically implantable drug delivery devices have been developed and patented, and are discussed below.

U.S. Pat. Nos. 6,217,895; 6,001,386; 5,902,598; and 5,836,935, Ashton et al. describe a surgically implantable device for local deliver of low solubility therapeutic agents in an internal portion of the body. The device comprises an inner core containing the drug isolated from the surrounding environment by a permeable coating polymer which controls the release rate of the drug. The device delivers the drug in a multidirectional way from the implantation site, exposing all the structures in the site to the delivered agent. Moreover, the drug release occurs and is through a complex technology of a coating polymer that is non-bioerodible and permeable to the drug.

U.S. Pat. No. 4,378,016, to Loeb, describes a surgically implantable device for delivering an active factor to a mammalian site. The device comprises a fluid permeable membranous sack for implantation within the mammal and an impermeable hollow tube having one end connected to an opening in the sack and the other end designed to remain outside the body of the mammal. The tube provides an access passageway to the membranous sack, such that after the sack has been surgically implanted into the mammal, a cell-containing envelope may be introduced into the sack via the tube. Upon insertion of the cell-containing envelope into the sack the cells may produce an active factor which subsequently may diffuse into the surrounding tissue or organ of the recipient.

U.S. Pat. No. 5,182,111, to Aebischer et al., describes a surgically implantable device for delivering an active factor to a pre-selected site, for example, a tissue or organ in a mammal. The device comprises a semi-permeable membrane enclosing at least one cell type that produces a specific active-factor and a second cell type that produces an augmentory factor. The augmenting factor produced by the second cell type subsequently induces the first cell type to produce the active-factor.

U.S. Pat. No. 4,479,796, to Kallok, describes a surgically implantable dispenser for infusing a pre-selected drug directly into the blood stream. Briefly, the dispenser is surgically spliced in line with a blood vessel. The dispenser encloses a replaceable cartridge of cells, micro-organisms, which produce and secrete the drug into blood flowing past the cartridge.

U.S. Pat. No. 4,309,776, to Berguer, describes an intravascular drug delivery device having a chamber containing transplanted cells for surgical implantation into the wall of a blood vessel. The device comprises a porous wall that permits a hormone produced by the transplanted cells to diffuse out of the chamber and into the blood stream U.S. Pat. Nos. 6,251,090; 5,830,173 and 5,725,493, to Avery et al., describe a drug delivery device, comprising a refillable reservoir connected to the vitreous cavity through a tube. This concept requires intraocular invasion, which limits its application to situations when the integrity of the targeted tissue is not an issue.

U.S. Pat. Nos. 6,416,777 and 6,413,540 disclose a device that once positioned underneath the Tenon's capsule, in contact to the sclera, is supposed to deliver agents to the eye. Such system is composed of an outer layer impermeable to the delivered therapeutic agent, diminishing its wash out by the periocular fluids. The device has a geometry that facilitates its insertion and placement in the sub-Tenon's space, and reference is made to a method to place and hold it under the inferior oblique muscle, avoiding its dislocation from its original location and proportioning its positioning near the macula area. No references are made to methods to hermetically seal it to the sclera or to the targeted tissue. Moreover, the design of those devices does not accommodate methods to carry more than one agent, as in a bi-compartmental reservoir neither it refers to refilling ports to allow reposition of the liquid therapeutic agents.

The necessity of the use of a hermetically sealed device arises from characteristics determined by the drugs and tissues. Among the drug-related factors are: narrow difference in the efficacious-toxic concentration; high instability or susceptibility to inactivation before reaching the aimed tissue; the requirement of prolonged and steady release curves, particularly in chronic diseases; and availability in liquid or gel state. The tissue factors are mainly related to the level of topographic specificity that is required from that agent, and not less importantly to the harms and susceptibility of the surrounding tissues to the drug toxic effects.

The possibility of drug leakage through the device-tissue junction sharply excludes the use of some important therapeutic agents, not only cytotoxic drugs, but other more specific agents. Angiogenic peptides could never be applied and exposed to other tissues other than where aimed to act. If aimed to the choroid by increasing the blood flow and stimulating capillary growth, its possible exposure to the vascularized periocular tissue before even crossing the sclera, beyond dissipating the angiogenic effect, could increase the flux of blood and plasma around the implant and speed up the degradation or neutralization of its active agent. Moreover, biological processes occurring in that location may alter significantly the release pattern of any agent from the delivery device whether the agent is still active or not.

Inflammatory reactions are the basis of the healing process in mammalians, involving the release of a wide range of chemical, biological and cellular factors that ultimately lead to a reorganization of the tissue. Scar formation and foreign body reactions are common responses from an organism to traumatic and surgical injuries, particularly if there is exposure to inert or immunogenic materials. These responses are created to reconstitute the affected or exposed tissue through a series of reactions that frequently culminate with strengthening of the affected tissue and isolation or extrusion of the foreign body.

Over the past decades significant experience with periocular implants has been achieved through the well established practice of encircling elements for treating retinal detachment and by the proliferation of filtration devices for the surgical therapy of glaucoma. Many polymers were tested for that purpose and the experience accumulated over the years showed that the encapsulation of the implant invariably happens after periocular implantation. Indeed, even for largely used medical products such as silicone, it was shown that the encapsulation process starts as soon as 3 days following insertion. Nevertheless, a fibrotic reaction to a prosthesis or to a structural implant is not so harmful. Instead, it is even desired to provide mechanical stability to the implant and enhance its structural function[19,20,21,22].

The lack of a way to hermetically seal the device to the tissue would not only affect the way the carried agent would act and react with the surrounding tissues, but also the way the surrounding tissues would respond to the agent and the system. The encapsulation of such system, and the formation of a layer of scar tissue between the drug reservoir and the organ surface would change significantly the pattern of drug release altering the main determinants of diffusion through that surface, which is primarily composed by a membrane with known characteristics, and diffusion coefficients for certain molecules.

In Ophthalmology, several studies were carried out to characterize the sclera, the most external layer of the eyeball, as a membrane. Many experiments justified the use of periocular injections to deliver drugs to the eye. Edelhauser et al. studied extensively the properties of the sclera as a permeable membrane. His in vitro studies were further enhanced by in vivo studies to show how periocular injections can deliver agents to the internal eye tissues. It was shown that molecules as large as 70 KDa can diffuse across the sclera and reach the intraocular space, even against a pressure gradient. Such properties are partially explained by porous characteristics of the scleral collagen, although the whole mechanism is still not totally understood, particularly the mechanisms these large molecules can reach the intravitreal space, bypassing tight junctions of very selective barriers such as the outer blood-retinal barrier. Indeed, the unprotected transcleral route has been used for many years and has proved to be effective with the administration of certain drugs. Anti-inflammatory steroids are injected through the conjuctiva into the subTenon space and put directly in contact with the sclera, which allows the diffusion of the drug toward the intraocular space, providing high therapeutic levels of the drug to the various layers of the eye. Deposit formulas of steroids are available with demonstrated safety and equivalency, or superior effectiveness to the systemic route, but without its inconvenient side effects. However, because these injections are unprotected from the surrounding orbital tissue, much of the injected dose is absorbed systemically and carried away from the site. The therapeutic effect is short-lived[7,8,9].

Some other drugs cannot be administered by this periocular route because of significant irritation and toxicity to the adjacent tissues at the high levels necessary to permeate the layers of the eye. High concentrations of agents are necessary because of dissipation of the drug in the periocular tissue. This is mainly attributed to a washout mechanism by the periocular soft tissue or inactivation of the agents by inflammatory cells, immunoglobulins and plasma components before they reach the targeted structure.

In certain conditions, such as in endophthamitis, the intraocular use of the drug is appropriate by providing high levels of the antibiotic available in a short period of time. However, for chronic use, repeated intraocular injections bring an unnecessary high risk of complications, either from the injection procedure or from high drug concentrations instantaneously provided by the direct injection. Intraocular procedures are not always possible. Inflammatory conditions such as uveitis, particularly in the severe disorders, such as in Behcet's disease, even minimally invasive intraocular procedures can lead to a severe and prolonged hypotony. Intraocular cancers also require non-invasive approaches due to the risk of cancer cells being disseminated throughout the orbit. Retinoblastoma, most common primary intraocular tumor in childhood, is an ideal disorder for the local delivery of chemotherapeutics. One of its clinical presentations, characterized by seeding of tumor cells in the vitreous gel, is currently treated by systemic chemotherapy. The failure of systemic treatment is frequently due to limited achievement of therapeutic levels of the drugs in that location, and often leads to removal of the eye. Administering the drug directly into the vitreous is impossible because of the risk of tumor cell dissemination, directly leading to death.

Regional therapy is an alternative and is currently under clinical trials. Promising efficacy has been achieved but some toxic side effects were reported as well. In this specific situation high levels of cytotoxic drugs, such as carboplatin in the orbit, can result in unpredictable side effects during the patient's lifetime, particularly in the retinoblastoma population which is more susceptible to secondary neoplasias due to gene mutations. Similar therapeutic levels of the drug in the eye could be achieved if the periocularly injected drug was isolated or protected from the extraocular connective tissue, which offers potential advantages of prolonged release time and certainly fewer side effects to the orbital structures and optic nerve. Furthermore, a controlled release of those agents could be achieved since the interface area with the drug is well defined, a main predictor of drug diffusion rates across the sclera. The positioning of the drug in contact with a specific area of the sclera would also avoid exposure of more sensitive structures, e.g. optic nerve, to potentially toxic drugs at high concentrations.

Regional therapy has been extensively studied and has proved to be efficacious in several conditions. Although drug delivery systems based on polymer technology have improved the bioavailability and pharmacokinetics of therapeutic agents in the targeted sites, lack of local specificity is still a major limitation to its clinical applicability.

New classes of therapeutic agents have demonstrated promise, but the inability to efficiently and specifically deliver such agents to the target limited the achievement of successful results to the in vitro studies. A number of those when tested in vivo, fail to produce the same results as in vitro.

Moreover, tumor cells as well as infectious agents can spread to other organs or even systemically, once the natural barriers of the organ are surgically broken. The systems aforementioned, when not delivering the agent directly to the interstice of the aimed tissue, can still provide therapeutic levels by releasing the agent to the cavity or the surrounding space and fluids. This ultimately can lead to uptake from the organ and from any of the adjacent structures. Such perfusion systems lack specificity and are not suitable for clinical use when the drugs are toxic to the surrounding structures. This problem becomes more prominent when the agent may trigger other pathologic processes. This is more frequent when using viral gene vectors, inhibitors of biological factors and non-specific sensitizers.

Patched delivery systems have been developed for transdermal or transmucosal release of drugs. Such systems are designed to have one interface with the dermal or mucosal epithelium through which the diffusion of drug occurs. The other interface is usually external of the target body tissue, e.g. the external environment in the case of a transdermal patch, or the intestinal lumen or oral cavity, in transmucosal models. The main concern in designing those devices is to protect the carried agent from the secretions of the gastrointestinal, oral and nasal tracts and consequently to allow more drug to reach the systemic circulation, instead of directly acting in a targeted organ or tissue[1,2,3].

With transmucosal devices any release from the external surface will be neutralized by luminal enzymes, flora or physical inactivation, or will reach the systemic circulation after distal absorption what is ultimately the goal of most of these drug delivery systems. Neither transdermal or transmucosal delivery systems were conceptualized to be surgically implanted nor designed to meet the level of biocompatibility necessary to be exposed to internal body fluids, e.g. blood, connective tissue, or any internal cellular response. Their application is under exposure to body secretions, therefore, they are not usually subject to severe inflammatory reactions and do not require high levels of biocompatibility, factors that make them unsuitable for surgical implantation[1,2].

Systems like polymer shields for drug release as the ones available for ocular use, share some of the characteristics of the transdermal and transmucosal systems. They do not aim to deliver the drug directly to the cornea or conjunctiva or to any specific ocular structure, but release the agent to a body secretion fluid as the the lacrimal film, in a multidirectional way. From the tear film agent diffusion occurs throughout the ocular surface and later to the lacrimal drainage system and nasopharyngeal mucosa, again exposing other tissues to side toxic effects. These systems can provide a sustained release of an agent, but in a non-selective way, dissipating its effects to all the surrounding structures, e.g. conjunctiva, lid skin, cornea, lacrimal system. As with the transdermal and transmucosal systems, those systems were designed to offer the advantage of non-invasive sustained release, not be implanted through surgical procedures, but just attachment to body or mucosal surfaces.[4,5]

Experimental and clinical evidences suggest that organ surfaces exposed to high levels of drugs can lead to internal therapeutic levels even higher than those achieved by systemic administration. The potential diffusion properties of organs and tissues are discussed, as well as the advantages of its exploration as a therapeutic route.

Bioactive peptides are agents necessary and naturally present in biological process, but may also be undesirably present in pathogenic situations, e.g. tumors, choroidal neovascular membranes, and absent as well, e.g. ischemic areas of the myocardium. The over or down regulation of such factors can lead to the improvement of pathologic conditions, and their efficient use as therapeutic agents, require the ability to provide to the target tissue the desired quantity in a sustained and prolonged fashion. The same protected regulated delivery is required for gene vectors, antisense agents, antibiotics, cytotoxic drugs, enzymes, certain hormones, etc. Other agents known as sensitizers also require a specific action, and the drug uptake by the targeted tissue will later define the efficiency of the definitive treatment, e.g. chemo, laser, radio or thermal therapies, in restricting and enhancing its effects, as well as side effects, to that site.

Local drug delivery is also under clinical studies for the treatment of intracranial tumors. Some neural origin tumors, such as malignant glioma have received most of the attention. These tumors are treated by a standard combination of surgical resection and external beam radiation. Due to the ability of this tumor to invade the normal adjacent brain it often recurs in the adjacent margins of resection. Based on those characteristics and the tumor unresponsiveness to systemic chemotherapy, the local delivery of drugs, sensitizers and peptide vectors started to be considered and studied as a treatment option, with potential effects on the quality of life of affected subjects.

Brem et al. have reported prolonged survival using polymers containing BCNU in controlled trial for recurrent glioblastoma. Such polymers are prepared to release 50% of the drug in the first 24 hours, and 95% by 120 hours[10,11].

Another study reported a high incidence of perioperative complications, such as wound infection and seizures, without showing advantages over the conventional treatment[12]. Exposing tissues to higher concentrations of a therapeutic agent increases the chance of a greater efficacy without systemic side effects, but also increases the risk of local side effects, usually dose-related.

The prior art did not recognize that a selective and protected local delivery system could substantially improve the effectiveness of the treatment, as well as make available other agents never accepted for that use because of potential toxicity to the adjacent structures, and prior art systems designed to deliver drugs to the site where they are implanted provide no protection for other sensitive normal structures nearby.

For example, regional therapy to deliver bioactive agent to the myocardium and epicardial space has been extensively explored. Pericardial effusion syndrome and metastatic tumors were shown to respond very well to local delivery of chemotherapeutics by intrapericardial perfusion of 5-Fluorouracil and cisplatin through a catheter. This technique is efficacious in providing the epicardium space with high levels of drug, but imposes the risk of secondary infection if used in a chronic basis.[13,14]

An elegant study by Darsinos et al. showed the pharmacokinetics of digoxin and lidocain in the various heart tissues, including valves. Their study showed that these compounds follow an irregular distribution among cardiac tissues, after pericardium injection. Again, specificity of an agent to a determined region of the same organ is desirable for conditions such arrythmias and dysfunctional cardiopathies. Absorption of digoxin by the atria and absorption of both drugs by intrapericardial aorta were higher than that of other heart tissues, between 20 and 60 minutes. At 30 and 60 minutes, lidocaine was evenly distributed across the LV wall while digoxin 50 micrograms was mainly concentrated subepicardially. This distribution limits the intrapericardial route for administering those agents to situations where higher levels in those areas are desired[15]. The same author showed in another study that the concentration of amiodarone injected into the pericardium was higher in the subepicardium compared to deeper layers of the left ventricule, without measurable concentration in the blood[16]. The preferential distribution of those agents is due to an increased uptake of the drug by certain areas. Since this injection exposes the whole area of the myocardium surface to the agent, it is susceptible to different uptake rates between regions, and consequently to a non-controlled preferential delivery.

The effectiveness of bioactive agents as therapeutics depends on their delivery routes. For some bioactive reagents, their natural biological occurrence make them subject to inactivation or saturation by a variety of factors normally present in fluids and tissues before they reach their targets. Some growth factors and other compounds were shown to increase the vascularization of infarcted areas of the myocardium. Uchida et al. showed in a dog model of myocardial infarction, that the transcatheter intrapericardial injection of basic Fibroblast Growth Factor (bFGF) plus heparin sulfate is effective in causing angiogenesis and myocardial salvage more in the subepicardial infarcted area than in the subendocardial area. Further studies done in porcine model of chronic myocardial infaction confirmed the effectiveness of intrapericardial injection of b-FGF in inducing vascularization of myocardium.[17,18]. Although this shows promising results in animal studies, it is still questionable whether this route will be feasible in patients with prior instrumentation, including bypass surgeries.

The intravenous route was also considered and clinically studied, but did not show benefits compared to placebo. The use of this delivery route imposes concerns about a potential acceleration of retinal vascular diseases and occult neoplasias.

Vascular growth factors tend to bind to their receptors or be inactivated, so they are subject to saturation before reaching deeper layers of the tissues. Consequently, if vascular growth factors are unequally distributed among different layers of the tissue, their effects are expected to be as well. To allow them to reach deeper layers of the myocardium, it is necessary to protect them from unaffected areas, and limit their action to a defined pathologic area, where they will have a better chance to reach deeper after a longer period of exposure. A method for delivering the agent in a localized, sustained, protected and very selective manner, would more likely perform those tasks, with less side effects, through a minimally invasive implantation procedure, potentially benefiting a significant affected population that is not eligible for more morbid procedures. This strategy offers the advantages of the intrapericardial procedures, with comparable efficacy to intramyocardial approaches.

The use of bioactive agents locally has been subject to a number of studies. Inhibitors of vasculogenesis are potential tools for treating angioproliferative eye diseases such as retinopathy of prematurity and age-related macular degeneration, two leading causes of blindness in premature newborns and the elderly population.

BACKGROUND SECTION USPTO DATABASE

U.S. Pat. Nos. 6,217,895; 6,001,386; 5,902,598; and 5,836,935, Ashton et al.
U.S. Pat. No. 4,378,016, to Loeb
U.S. Pat. No. 5,182,111, to Aebischer et al
U.S. Pat. No. 4,479,796, to Kallok
U.S. Pat. No. 4,309,776, to Berguer
U.S. Pat. Nos. 6,251,090, and 5,725,493, to Avery
U.S. Pat. Nos. 6,416,777 and 6,413,540, to Yaacobi et al.

BACKGROUND SECTION REFERENCES

1. Torres-Lugo M, Peppas N A: Transmucosal delivery systems for calcitonin: a review. Biomaterials 2000 June; 21(12):1191–6.
2. Benes L, Claustrat B, Horriere F, Geoffriau M, Konsil J, Parrott K A, DeGrande G, McQuinn R L, Ayres J W: Transmucosal, oral controlled-release, and transdermal drug administration in human subjects: a crossover study with melatonin. J Pharm Sci 1997 October; 86(10):1115–9.
2. Sayani A P, Chien Y W: Systemic delivery of peptides and proteins across absorptive mucosae. Crit Rev Ther Drug Carrier Syst 1996; 13(1–2):85–184.
4. Gebhardt B M, Kaufman H E: Collagen as a delivery system for hydrophobic drugs: studies with cyclosporine. J Ocul Pharmacol Ther 1995 Fall; 11(3):319–27.
5. Kanpolat A, Batioglu F, Yilmaz M, Akbas F: Penetration of cyclosporin A into the rabbit cornea and aqueous humor after topical drop and collagen shield administration. CLAO J 1994 April; 20(2):119–22.
6. Lehr C M: From sticky stuff to sweet receptors—achievements, limits and novel approaches to bioadhesion. Eur J Drug Metab Pharmacokinet 1996 April–June; 21(2):139–48.
7. Rudnick D E, Noonan J S, Geroski D H, Prausnitz M R, Edelhauser H F: The effect of intraocular pressure on human and rabbit scleral permeability. Invest Ophthalmol Vis Sci 1999 November; 40(12):3054–8.
8. Olsen T W, Aaberg S Y, Geroski D H, Edelhauser H F: Human sclera: thickness and surface area. Am J Ophthalmol 1998 February; 125(2):237–41.
9. Olsen T W, Edelhauser H F, Lim J I, Geroski D H: Human scleral permeability. Effects of age, cryotherapy, transscleral diode laser, and surgical thinning. Invest Ophthalmol Vis Sci 1995 August; 36(9):1893–903
10. Brem H, Piontadosi S et al.: Placebo controlled trial of eficaccy of intraoperative controlled delivery of biodegradable polymers of chemotherapy for recurrent gliomas. 1995, Lance 345: 1008–1012.
11. Trials of local delivery of chemotherapy as first line treatment for malignant gliomas were also conducted, at this time using interstitial application of chemotherapeutics impregnated polymers. The results were promising, showing a prolonged survival in the treated group. (Valtonen S, Timonen U, Toivanen P, Kalimo H, Kivipelto L, Heiskanen O, Unsgaard G, Kuurne T: Interstitial chemotherapy with carmustine-loaded polymers for high-grade gliomas: a randomized double-blind study. Neurosurgery 1997 July; 41(1):44–8; discussion 48–9.
12. Subach B R, Whitam T F: Morbidity and survival after 1,3-bis(2-chloroethyl)-1-nitrosurea wafer implantation for recurrent glioblastoma: a retrospective case-matched cohort series. 1999 Neurosurgery 45: 17–22.
13. Tabeta H, Watanabe R, Kimura H et al.: Controlling malignant pericardial effusion by intrapericardial carboplatin administration in patients with primary non-small-cell lung cancer. Br J Cancer. October; 83(7):858–62., 2000.
14. Lerner-Tung M B, Chang A Y, Ong L S, Kreiser D.: Pharmacokinetics of intrapericardial administration of 5-fluorouracil. Cancer Chemother Pharmacol 1997;40(4): 318–20.
15. Darsinos J T, Samouilidou E C, Krumholz B, Kontoyanni M, Pistevos A K, Karli J N, Theodorakis M G, Levis G M, Moulopoulos S D: Distribution of lidocaine and digoxin in heart tissues and aorta following intrapericardial administration.Int J Clin Pharmacol Ther Toxicol 1993 December; 31(12):611–5.
16. Darsinos J T, Karli J N, Samouilidou E C, Krumbholz B, Pistevos A C, Levis G M: Distribution of amiodarone in heart tissues following intrapericardial administration. Int J Clin Pharmacol Ther 1999 June; 37(6):301–6.
17. Uchida Y, Yanagisawa-Miwa A, Nakamura F, Yamada K, Tomaru T, Kimura K, Morita T: Angiogenic therapy of acute myocardial infarction by intrapericardial injection of basic fibroblast growth factor and heparin sulfate: an experimental study. Am Heart J 1995 December; 130(6): 1182–8.
18. Laham R J, Rezaee M, Post M, Novicki D, Sellke F W, Pearlman J D, Simons M, Hung D. Intrapericardial delivery of fibroblast growth factor-2 induces neovascularization in a porcine model of chronic myocardial ischemia. J Pharmacol Exp Ther 2000 February; 292(2):795–802.
19. D'Hermies F, Korobelnik J-F, Chauvaud D, Pouliquen Y, Parel J-M, Renard G: Scleral and episcleral histological changes related to encircling explants in 20 eyes. Acta Ophthalmol Scand. 1999: 77: 279–285.
20. D'Hermies F, Korobelnik J-F, Caputo G et al.: Encapsulation of Scleral Buckling Materials. A Study of Sixty Specimens. Ophthalmology, 1998: 105(6): 1079–1086.
21. Ricci B, Ricci F: Octyl 2-cyanoacrylate tissue adhesive in experimental scleral buckling. Acta Ophthalmologica Scand. 2001: 78: 506–508.
22. Korobelnik J F, D'Hermies F, Chauvaud D et al.: Expand Polytetrafluoroethylene Episcleral Implants Used as Encircling Scleral Buckling. An Experimental and Histopathological Study. Ophthalmic Res 2000; 32: 110–117.

In view of the foregoing, it is desired to have drug delivery devices that directly interface with a target tissue, with no or minimal drug being released to nontarget tissues.

SUMMARY OF THE INVENTION

In an embodiment, an implantable and sealable drug delivery system is provided, that provides local sustained release of a therapeutic agent or agents directly and selectively to a mammalian internal organ, tissue or system. A preferred embodiment comprises an isolated drug reservoir that solely delivers the agent through an interface that can be selectively exposed with the targeted structure. The control over the interface is achieved by a sealing mechanism provided by a sealing base and methods described therefore.

A simple and novel method of providing local or systemic therapeutic levels through a direct, unidirectional and protected delivery of agents to a mammalian organ, tissue or system is also disclosed. Devices of the present invention can deliver therapeutic agents to specific tissues surrounded by internal body fluids in a preferential manner, exposing only the targeted sites to high therapeutic levels of the agent for a prolonged period of time, and avoiding undesired toxic effects to adjacent structures.

In an embodiment, the drug reservoir is isolated from adjacent structures and fluids by an outer layer of polymer impermeable to the carried therapeutic agent. A delivery port or interface window is provided in the housing of the device for providing targeted release of a drug contained therein. The interface window is sealed to the tissue surface by a surrounding sealing base associated to designed structures to assure the hermetical seal necessary for the control of the interface diffusion mechanism. The delivery port or interface window may be covered by a structural layer that is permeable to the therapeutic agent contained within the device reservoir, or by a layer that is biodegradable. In certain instances, the therapeutic agent is contained in a slow release formulation that does not require that the delivery port or interface window be covered during implantation, so that a portion of the agent bolus in the device reservoir is directly contacted with the target tissue. In an embodiment, the device housing includes an attachment mechanism for attaching the device to a target tissue. This is provided by a series of structures that in combination allow a hermetical seal between the system and the targeted tissue.

This invention can provide therapeutic or prophylactic levels of therapeutic or physiological agents to mammalian organs, tissues or systems. This invention to provide sustained levels of physiological or therapeutic agents to artificial organs, cell cultures, cell or tissue scaffolds and transplanted organs or tissues. This invention can be used to implant through minimally invasive procedures a foldable, elastic, flexible or expandable drug delivery device to provide selective delivery of therapeutic or physiological agents to mammalian organs, tissues or systems, through a sustained and protected release of an agent, assuring an unidirectional diffusion through the target interface, and avoiding dissipation of the agent to adjacent structures. The invention can also provide to a mammalian organ or tissue a selective delivery of sensitizers, magnetic or radioactive agents that will offer benefits in treating or diagnosing those structures. The present invention may be better understood by reference to the figures and further detailed description below.

BRIEF DESCRIPTION OF THE DRAWINGS

FIG. 8. Lateral view of a human eye and schematic representation of the invented system and the method for its use FIG. 9. Angled superior view of the device and its relation to a tissue or organ surface FIG. 10. Angled inferior view of a single cavity device and its relation with the sealing base and coating adhesive FIG. 11. Cross-sectional schematic representation of the device, its relations to an organ surface and methods for accomplishing a hermetical sealing to its target FIG. 12. Cross-sectional schematic representation of the device applied to the eye FIG. 13. Cross-sectional schematic representation of the device applied to the eye and methods for refilling its reservoir FIG. 14. Angled inferior view of the invented system and relations between its reservoir, refilling port, suture stabilizer and sealing base FIG. 15. Angled superior view of the invented system and relations between its refilling port (distinguishable from the outer surface), the reservoir and the sealing base FIG. 16. Angled superior view of the invented device applied to an organ surface and the method for hermetical sealing of its base to tissue by way of a surrounding suture through designed roles in its base FIG. 17. Lateral view of a system applied to the scleral surface of an eye and the method of providing hermetical sealing of its base to the target tissue FIG. 18. Encircling band stabilizer designed to hold a buckle and maximize the sealing of the device's base to the tissue's surface FIG. 19. Lateral view of the device applied to the eye and the method to achieve sealing to the scleral surface through the use of a encircling element FIG. 20. Posterior and cross-sectional view of the device applied and sealed to sclera of a human eye by using a encircling element FIG. 21. Inferior view of the device with a coating layer of a structural biodegradable polymer to provide stability to the reservoir contain, surrounded by an adhesive layer FIG. 22. Angled inferior view of the device and relations between the inner biodegradable layer and its association to sealing structures such as the suture stabilizer and surrounding coating adhesive FIG. 23. Cross-sectional view of the device, comprising an inner biodegradable layer, a sealing base and a bioadhesive coating, and its microscopic relations to the sclera.

DETAILED DESCRIPTION OF THE DRAWINGS

Figure 1:
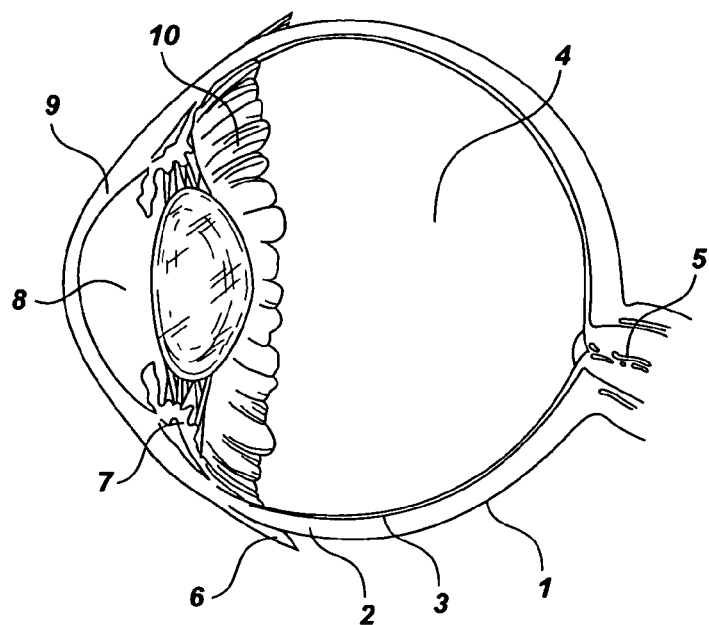
FIG. 1. Cross-sectional schematic view of the eye

The present invention relates to the field of local delivery device. The system described is intended to be used for treating diseases or conditions in mammalian organisms where a local delivery of therapeutic factors or agents are desired. The system was designed to be applied to a tissue or organ surface and there perform its function of releasing therapeutic agents. The invention consists on a device that provides very controlled conditions for therapeutic agents to permeate and distribute to an organ or tissue layers. Methods for achieving its functions comprise designed structures that allow a drug reservoir to be hermetically sealed to the target surface, keeping the characteristics that dictate the diffusion pattern of the drug constant for a prolonged period of time. The embodiment also incorporates structures to allow prolongation of its effective life by replacement or refilling with the therapeutic agent and use of more than one agent.

The invented system was designed to be applied to any surface of any organ or tissue surface. The drawing is a representation of its application to the eye, although the same methods are expected to be use for other tissues.

The FIG. 1 shows a schematic representation of the human eye. The relation between the diverse structures is important for understanding the application of the described system.

The eye is delineated anteriorly by the cornea (9) and posteriorly by the sclera (1). The cornea (9) is covered by the lacrimal film and exposed to the environment, while the sclera is surrounded by periocular tissue (6), including Tenon's capsule and extraocular muscles. The sclera relates to the posterior segment of the eye and the cornea to the anterior, each being separated from the other by the lens and mainly formed by a cavity. The cavity is filled anteriorly by aqueous humour (8), and posteriorly by the vitreous gel (4). In certain conditions the vitreous gel is replaced by aqueous humor or synthetic substitutes, such as silicone oil or gas. The aqueous humor is produced by the cilliary body (7). The impairment of the aqueous outflow leads to ocular hypertension and lately to a condition called glaucoma. Interfering with the aqueous humor productions is one of the ways to decrease of the IOP. The vitreous gel is the remaining of some fetal structures, occupying most of the posterior segment volume and composed by water and a collagen-proteoglicans network that is not replaced during the life time. The sclera relates internally to the choroid (2) which is composed basically by network of vessels delineated from the retina by the Bruch's membrane, retinal pigment epithelium (RPE) basement membrane and the RPE. These last structures play vital importance in the vision processes for being closely related to the photoreceptors, the most internal layer of the retina (3). The choroid extends anteriorly to become the pars plana (10) at the level of the ora serrata. Choroid, pars plana, pars plicata and iris are all constituted of uveal tissue and the site of a number of inflammatory and infectious processes of the eye. The sclera is perforated posteriorly by the ganglion cells of the retina at a site called lamina cribosa. The retina axons extend to form the optic nerve, which is lately responsible to conduct the vision signaling to the visual cortex of the brain.

Figure 2:
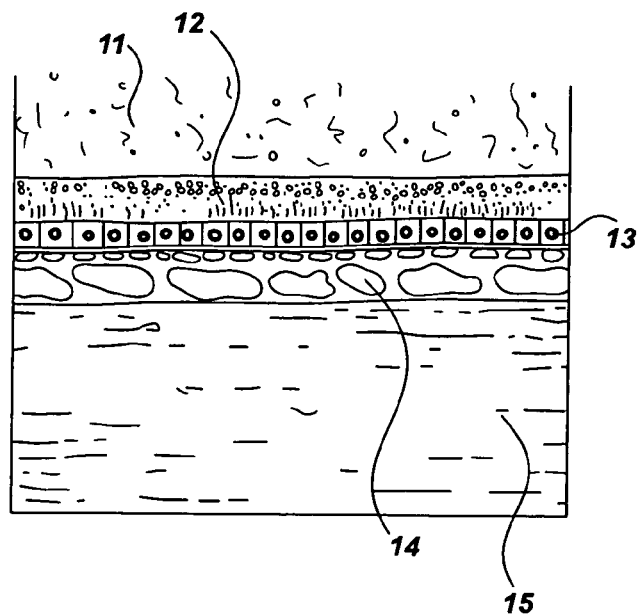
FIG. 2. Cross-sectional histological schematic view of the eye

FIG. 2. Schematic microscopic cross-sectional view of the eye layers, showing the correlation between the sclera (15), choroid (14), RPE complex (13), retina (12) and vitreous gel (11).

Figure 3:
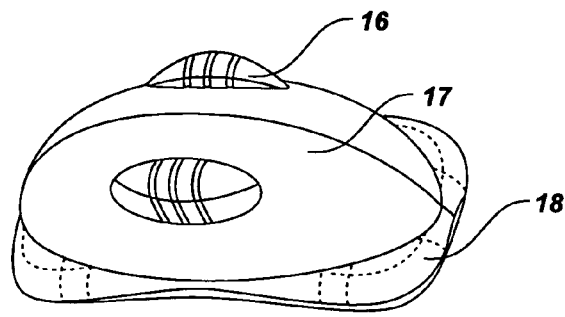
FIG. 3. Angled superior view of the invented device

FIG. 3. The invented device in an top-side view of its outer surface (17). The system comprises a reservoir-like body that is built in a polymer structure, preferentially but not limited to injection, compression, transfer and extrusion molding, depending on the polymer, co-polymer or matrix to be used. The choice of the polymer is driven basically by the characteristics of the organ or tissue to be implanted. It is preferentially made of but not limited to to poly-ethylene, silicone, hydrogels, poly-orthoester, poly-glycolic acid, poly-lactic acid, poly-caprolactone, polyvinyl-alcohol or any derivatives. The structure 16 is designed to stabilize the buckling suture. Sealing base 18 will maximize the hermetical seal to the target surface.

Figure 4:
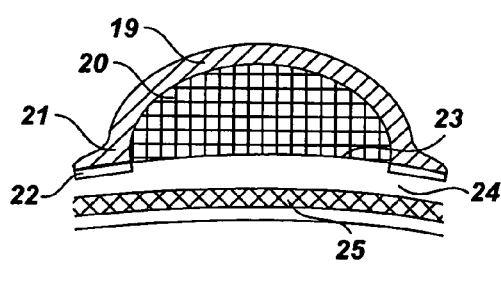
FIG. 4. Cross-sectional microscopic and schematic view of the device sealed to the eye FIG. 5. Cross-sectional schematic view of the device with a bi-compartmental reservoir FIG. 6. Inferior view of a bi-compartmental invented device, its sealing base and inner coating with a bioadhesive layer.

FIG. 4. The cross-sectional view of the embodiment comprised by the reservoir 20 containing the therapeutic agent. The external surface 19 continues with the sealing base 21, which will provide a hermetically sealed attachment with the target surface 24 through the use of an adhesive layer 22.

Figure 5:
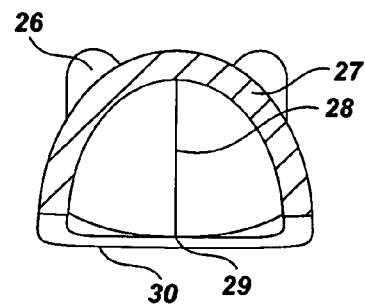

FIG. 5. The cross-sectional view of a bi-compartmental embodiment. The reservoir is divided by the internal wall 28, which extends beyond the curvature of the target surface, as shown by the art in 29, to provide a mild buckle or sealing effect with the tissue, and to avoid interaction between the agents before they reach the surface 30. The suture stabilizers 26 are also disclosed.

Figure 6:
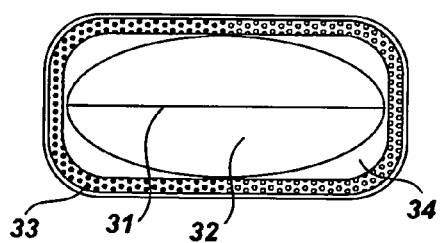

FIG. 6. The bottom view of the device showing bi-compartmental reservoir 32, the dividing internal wall 31, the sealing base 34 with a adhesive layer 33 applied to it.

Figure 7:
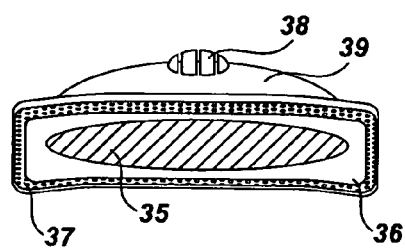
FIG. 7. Angled inferior view of the invented device, relations between suture stabilizer, reservoir, sealing base and adhesive coating.

FIG. 7. The bottom-side view of a single reservoir embodiment 35 and its relation to a sealing base 36, adhesive layer 37, external surface 39 and suture stabilizer 38. Preferentially, the internal curvature of the sealing base 36 follows the curvature of the target tissue.

FIG. 8. Example of application of the device 42 to an eye. In this case to illustrate in an eye containing an intraocular tumor called retinoblastoma, most frequent primary intraocular tumor during the childhood. The sclera surface 41 is exposed by peritomy and dissection of the adjacent tissue is performed. To better control the area of the sclera to be exposed the extraocular muscles 42 and 40 can be isolated by standard techniques. Once the sclera surface is clean of periocular tissue in that area, the implant 42, in this case carrying cytotoxic drugs, is held in place by the use of an applicator or just the hands. Sutures 45 are placed from one side of the implant to the other, having it crossing and fitting the stabilizers 44 to allow a mild buckle effect of the sealing base 42 and maximize its sealing effect. The sutures are passed through the scleral thickness. After the implantation the muscles are released and the conjunctiva is brought back to its original position covering the eye surface and sutured near the cornea.

FIG. 9. A top-side view of the implant 49 sutured to a tissue 46. The suture stabilizers 47 allow the sutures to hold the implant in place, but mainly creating a hermetical seal between the device and target surface.

FIG. 10. A bottom-side view illustrating the internal surface of the device that will be in contact to the sclera surface. The interface window 55 is surrounded by a sealing base 54. The sealing base 54 is coated in its most peripheral aspect by an adhesive layer 53.

FIG. 11. A cross-sectional view of the device applied to the tissue surface, showing the interface 60 between the reservoir and the tissue. The relations between the sealing base 58 and the target tissue are also disclosed. In this case the hermetical seal was achieved by using a adhesive layer 59 covering the base 58.

FIG. 12. A cross-sectional view of the device and target tissue 65 showing the interface between the sealing base 63 and the sclera 65 with a hermetical seal provided by the adhesive layer 64.

Figure 13:
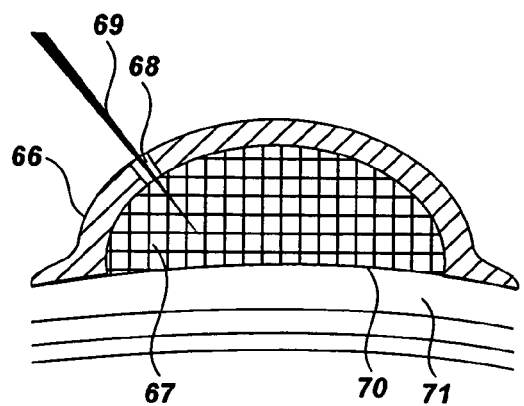

FIG. 13. A cross-sectional view of a single compartment 67 device in apposition to the sclera 71. The method for refilling the reservoir is disclosed. The external surface 66 of the device comprises a refilling port 68, made preferentially of self-sealing rubber. The drug, solution or suspension is injected through a cannula or needle device 69. A irrigation-aspiration device may also be used for aspirating any remaining solution and refilling the reservoir with the new solution or drug. The refilling port 68 is built in an angle to favor its localization and insertion of the needle 69.

Figure 14:
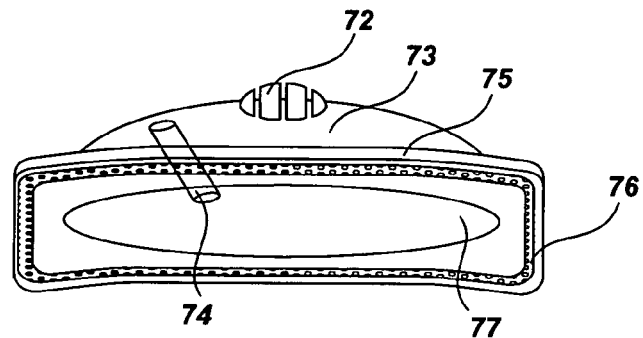

FIG. 14. A bottom-side view of the internal surface of the device, showing the relations between the sealing base 75, the adhesive layer 76, external surface 73, suture stabilizer 72, and a refilling port 74 communicating the external environment with the interior of the reservoir 77. The refilling port is preferentially made during the molding process for the external surface 72, and lately by a second process to incorporate the self-sealing rubber, preferentially but not limited to silicone, to the port cavity or hole. The location of the port 74 as well as its angle to access the reservoir 77 follow the most appropriate way to insert the refilling needle or cannula.

Figure 15:
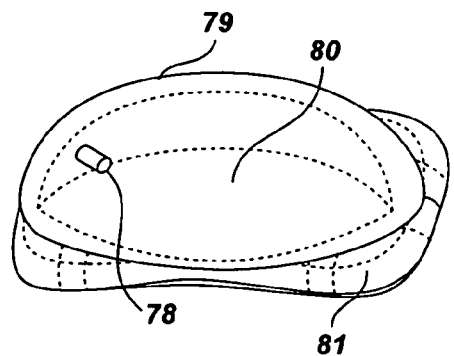

FIG. 15. The top-side view of the device illustrating the relation between the refilling port 78 and the outer surface 79. To improve the self-sealing performance, depending on the thickness of the external wall 79, it may be built angled in a way to increase the length of the tunnel and maximize the sealing properties of the port 78.

Figure 16:
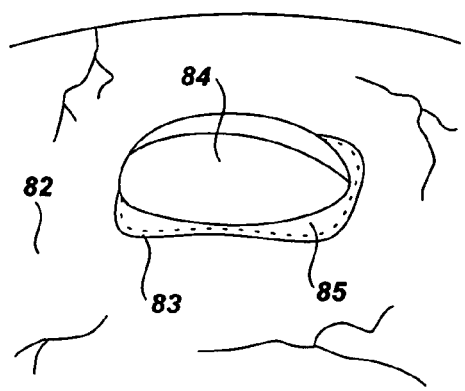

FIG. 16. Illustrates the relations between the device 84 and a tissue surface 82. Note that the sealing base 85 is perforated by multiple holes 83 to allow a sewing suture with a sealing effect on the base 85. A variation is to build a thinned tunnel along the surface of the sealing base and surrounding it and would suitable to continuous suturing by either a manual or automatic technique applied during the implantation surgical procedure.

Figure 17:
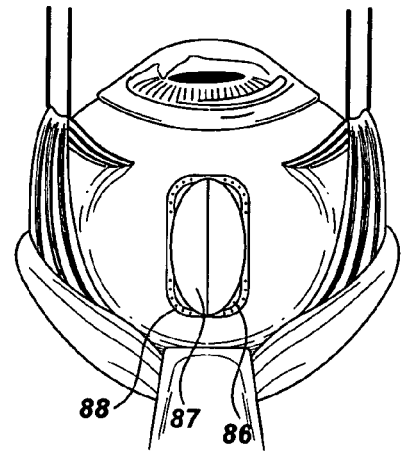

FIG. 17. Illustrates an example of application of the device 87 to the sclera surface of a human eye, where a sewing suture 88 was used to accomplish a sealing effect of the base 86.

Figure 18:
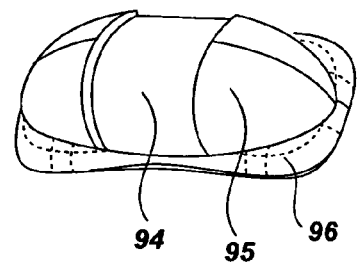

FIG. 18. Discloses an embodiment where a trail or tunnel 94 was built in the device external surface 95, crossing its diameter to provide a method for sealing the base to a target tissue. The trail 94 is aimed to be fitted by an encircling element, preferentially made, but not limited to silicone, although variations by using any king of explants are expected.

Figure 19:
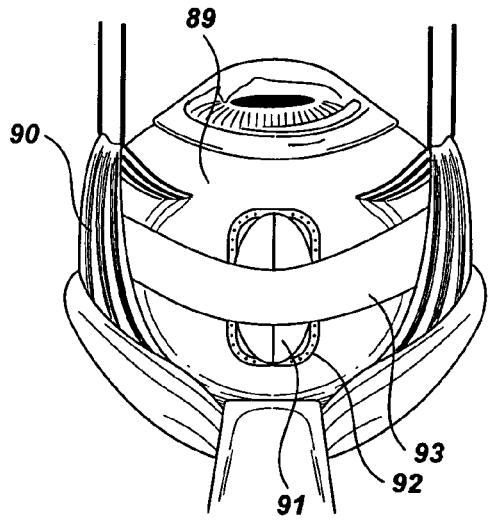

FIG. 19. Illustrates the application of the device 91 positioned in contact to the sclera 89 and underneath an encircling element 93. The encircling element 93 is placed by established techniques, associated or not to a procedure for retinal detachment treatment. Once the encircling element is tied up, the base 92 is expected to function as a hermetically sealed interface.

Figure 20:
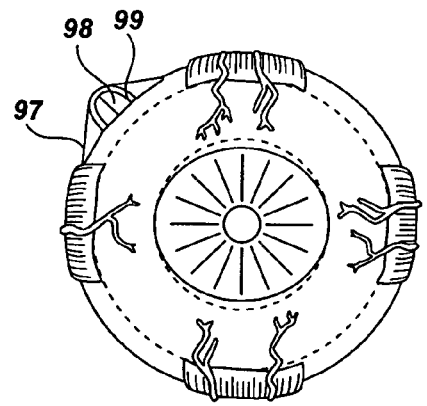

FIG. 20. Illustrates the application of the device 98, in this case bi-compartmental under a encircling element 97. A hermetical apposition 99 effect of the device against the sclera is achieved by this method. Furthermore, other device can be positioned anywhere underneath the encircling element, depending on the number and dose of the agents necessary for treating that condition.

Figure 21:
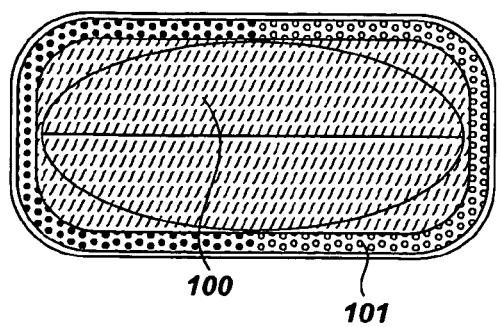

FIG. 21. Discloses a variation of the internal surface where a layer of biodegradable polymer 100 is applied to contain the agent inside the reservoir. The membrane is preferentially applied by apposition between the sealing a base and the adhesive layer 101. It is accomplished by creating a series of fenestrations along the most peripheral aspect of the biodegradable layer 100. Variations are expected and discussed hereinbelow.

Figure 22:
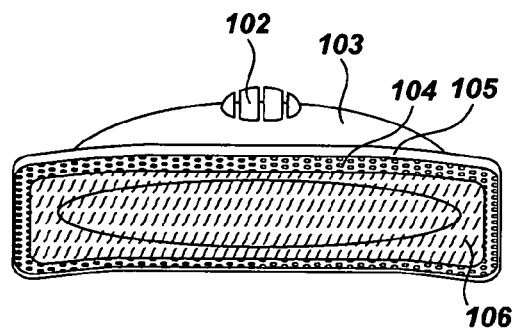

FIG. 22. The bottom-side view of the device illustrating the relations between the body 103, suture stabilizer 102, sealing base 105, biodegradable layer 106, and the adhesive layer 104.

Figure 23:
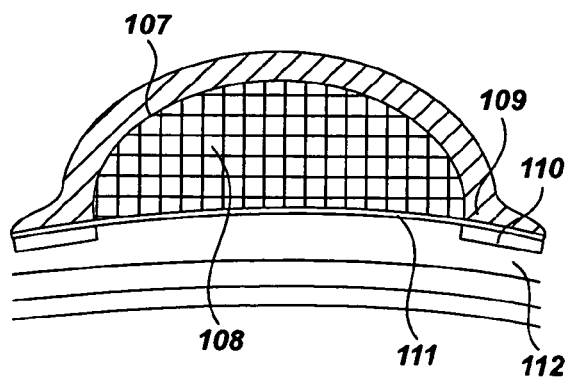

FIG. 23. Illustrates the cross-sectional view of the relations between the device and the ocular tissue. Here the device contains a single compartment 108 where the solution with the drug is located and held by a coating biodegradable layer 111 to prevent if from leaking or premature exposure before the hermetical seal is accomplished. The layer 111 is expected to play a structural function. Once it is dissolved the drug or agent will be exposed to the sclera and penetrate the eye layers.

DETAILED DESCRIPTION OF THE INVENTION

In an embodiment, the present invention involves a new method of selectively deliver therapeutic agents to mammalian organs, tissues or systems through a surgically implantable and hermetically sealable device system that provides a sustained and protected release of an agent, assuring an unidirectional diffusion through the target interface, and avoiding dissipation of the agent to adjacent structures.

The invention was based on unexpected findings that agents can be safely and predictably delivered at therapeutic or prophylactic levels to specific tissues, even in a local context, through the control of the organ surface exposed to an agent as well as by control of the agent's exposure to the internal body tissues and fluids. This can be achieved by maintaining the organ interface permeable to the agent through osmotic agents, physical, chemical or biological treatment, and by isolating and localizing the interface area of exchange through a sealing mechanism.

The control of the agent exposed to the targeted tissue can be obtained by using drug-associated polymers, osmotic agents and by preferably by coating the drug reservoir with a non-drug-permeable polymer, wherein the drug to which the polymer is not permeable is the active agent(s)), avoiding dissipation and toxic effects of the agents to adjacent structures and fluids, and higher availability to the targeted structure. This is proportioned by a series of structures designed to maintain a hermetically sealed contact between the device and the target tissue.

The inventors found that this system can offer a tremendous advantage over the conventional way the drugs are delivered to tissues or organs, allowing even agents never considered for clinical use due to non-specificity and toxicity to be reconsidered for use. This enables new agents to be developed based on this alternative of drug delivery technology.

This invention allows new therapeutic modalities, such as organ transplantation, tissue regeneration techniques, artificial organs or tissue implantation, to be developed. This will provide a therapeutic and physiologic support to any new technology that will depend on biological local incorporation or maintaining in an internal body portion.

Drug within the reservoir can be associated or mixed with another agent, a polymer or an osmotic agent. Layers of drug can be provided, wherein a first drug is delivered, followed by a second drug. A multi-compartmental reservoir is also designed having an inner wall separating the cavities. The body BI comprises the construction of a wall dividing the cavities. Preferentially the dividing wall slightly extends beyond the corresponding height to the curvature of the sclera or the surface to isolate the compartments at the interface level. It minimizes the possibility of mixture and interaction between the agents before they reach the target surface.

The interface window may have be coated and/or contain an enhancer of tissue diffusion, such as an enzyme. Collagenases, prostaglandin analogues, matrix metalloproteinases, hyluronidases are enzymes that can modify the diffusion properties of the sclera or tissue surface. The coating process is preferentially done when compressing the solid drug or during the drug preparation and mixture with its polymer or vehicle. If it requires a steady and sustained effect it can be dispersed throughout the reservoir or restricted to the internal surface to be place in contact with the sclera. Depending on the stability and interaction between the enhancer and the active therapeutic agent a layer of the enhancer may be incorporated to the internal surface of the reservoir. Preferentially it is made using a biodegradable material such as a collagen biomaterial, gelatin, glycolic acid, cellulose and lactic acid. Alternatively it can be made of any material that does not interfere directly in the release rate of the agent from the reservoir and its exposure to the target tissue. In other words, it is not the material carrying the enhancer expected to play a direct role in the diffusion rate, but the action of enhancer on the target surface. We refer to this layer as a functional layer for containing an agent or enhancer that will affect the diffusion rate and lately the pharmacokinetics of the given therapeutic agent.

An internal layer of a rapidly biodegradable polymer, preferentially a gelatin, hialuronic acid, methyl-cellulose, poly-glycolic, poly-lactic is envisioned to be built for allowing liquid, powder and viscous agents to be held in the reservoir it gets stable on the target surface. This process is preferentially accomplished by interpositioning the layer between the sealing base and the adhesive layer, in its more inner aspect, still allowing a strong adhesion between the adhesive layer and the sealing base in its most peripheral aspect. A tunnel surrounding the interface window is also envisioned to allow the entrapment of the layer in the tunnel using silicone or any material of the same class of the sealing base or the device to build a ring to be fitted in the tunnel by mechanical apposition or adhesive attachment.

The interface window, where the reservoir is exposed to the target tissue is surrounded by a sealing base that may be a continuation of the polymer composing the external wall or may constitute a different polymer incorporated to previous one by mechanical attachment or use of adhesives. The internal surface of the sealing base may also be composed by a different part, said sealing part, that once is mechanically incorporated to the main part, said the core device, can entrap a layer of polymer necessary to hold a liquid or viscous suspension in the reservoir avoiding premature exposure or leakage, or to stabilize the above described layer of enhancer carrier. The process is envisioned as a sandwich-like apposition still respecting the window area that will lately determine the interface between the drug reservoir and the target surface. The sealing part will then have the incorporated characteristics described above for the sealing base in order to allow hermetical sealing between the device and the exposed tissue.

Materials useful in constructing the device include but are not limited to poly-ethylene, silicone, hydrogels, poly-orthoester, poly-glycolic acid, poly-lactic acid, poly-caprolactone, polyvinyl-alcohol, polyvinyl-pylirridone, and any derivatives thereof, and biopolymers, such as hyaluronic acid, fibrin, methyl-cellulose, collagen, gelatin, or any derivatives might be used in other parts of the device.

Preferably, the device allows and protects the preferential flow of the therapeutic agent across the targeted interface. This is accomplished by using design structures to allow a hermetical sealing of the device to the target surface. Such unidirectional flow will be made possible by means of an external surface impermeable to the drug. Whether the external will be permeable or not to the external body fluids, will depend on the characteristics of the drug(s) and carrier polymer, as well as to the need for a dissolving agent to regulate the release of the drug from the reservoir. Such a mechanism of drug release may be as simple as the dissolution of the pure drug/polymer contained in the reservoir by the incoming fluids, or using an osmotic agent to regulate the water inflow and dissolution rate of the drug, before it permeates the targeted surface.

As mentioned before the embodiment incorporates a series of structures to allow a hermetical sealing to the target surface. The first is the sealing base, which consists on the primary way of achieving sealing. The extended surface beyond the interface window is aimed to increase the sealing contact area, whether or not it is coated with an adhesive layer. The sealing base preferentially follows the same curvature of the target surface, although a slightly more curved base is envisioned to maximize the contact, particularly when flexible materials are used. The combination of one or more or more of the other characteristics to ameliorate the sealing affect, said accessory sealing structures, will provide the characteristics for accomplishing the controlled and protected drug delivery.

The first accessory is described as a buckle suture stabilizer or suture stabilizer. This is a built bump, lane or tunnel on the external surface to prevent the suture to slide out of the implant once it buckles the device in apposition to the tissue. One or more can be built depending on the size and position of the device in relation to the target surface. Preferentially those suture stabilizers are made of the same material for the outer surface during the molding process. Alternatively, it can be incorporated to the device later on the process using different materials.

The second accessory is described as a buckling band tunnel or trail. It consists of a depression on the outer surface, crossing its diameter, to allow an encircling element to be place and provide a sealing apposition between the device and the target tissue. Preferentially it is built on the device external surface during the molding process.

The third accessory is described as a multiple holes base where a sewing suture should be applied to seal the base of the device. The holes again are preferentially created during the molding process for the sealing base. Alternatively a flexible material can be used as sealing base with a linear surrounding thinning to allow the suture to be performed by an automatic apparatus.

The above mentioned methods for creating a hermetical seal between the drug delivery device are essentials in diminishing the interference of surrounding fluid and tissues in the diffusion mechanism provided by the drug-tissue interface. Moreover, they play a significant role in avoiding unnecessary exposure of surrounding tissues to toxic effects of the pharmaceutical agents.

Fluid transport before drug dissolution occurs is possible through two distinct mechanisms. The first is across the organ surface through an osmotic or pressure gradient driven diffusion. The second is across the outer wall polymer mainly driven by an osmotic gradient between the reservoir and the outside tissue as well as the characteristics of the polymer.

Among the factors related to the permeation of agents through biological membranes, the surface contact area, concentration of the agent in the donor side and the molecular weight of the drug are balanced to provide the tissue with the desired levels of the agent in the specific regions. Other factors taken in account are the membrane properties and pharmacokinetics of the drug in the tissue. Those, despite being biological, can be altered through physical, chemical or biological methods, before the exposure to the therapeutic agent and device. In other words, the bioavailability and pharmacokinetics of the permeating agents are expected to be different through this proposed route, and will be helpful in establishing the appropriate combination of the compounds.

It is envisioned that the system of the present invention has numerous variations. For example, the device can carry an enhancer agent, preferentially, but not limited to an enzyme and a protein, such as albumin. The external surface can be composed by a polymer non-permeable to the carried agent, preferentially formed but not restricted to a silicone, poly-glycolic acid, poly-lactic acid, hyaluronate derivatives, polyvinyl alcohol, acrylate, methacrylate, cellulose, collagen, metals, any derivatives or associations of the above mentioned polymers or others that retain characteristics of non-permeability to the carried agent.

The external surface of the device may include a refilling port preferentially made of, but not restricted to a self-sealing material, such as silicone rubber. It is envisioned that in using a multiple compartmental device, multiple refilling ports are also built in the device. These structures are built on the external surface communicating the exterior environment to the interior of the reservoir. To be recognized after the surgical procedure the port is stained by a biocompatible, radiosensitive, echogenic marker or dye. Alternatively, its is also extended beyond the outer surface of the device and place in a more accessible part of the body.

The device may be foldable or flexible to allow insertion through small incisions, and to conform and tightly fit to irregular organs surfaces.

The invention includes methods for selective administration to a mammalian organ, tissue or system desired levels of a therapeutic agent through a controlled drug permeation across a target device interface. The interface with the tissue can be directly with drug contained within the device reservoir or through a biodegradable polymer, preferentially composed of but not restricted to gelatin, caprolactone, hyaluronic acid, cellulose, poly-glycolic acid, poly-lactic acid, and derivatives thereof. These compounds and/or compositions may be pressure, heat, photo, or chemically sensitive.

The active agents may be in an encapsulated form, such as liposomes or microspheres.

Thus, the present invention includes a method of local, protected and sustained delivery of therapeutic agents directly through a targeted tissue surface in a unidirectional way, avoiding dissipation of the agent to surrounding tissues and fluid, after surgical implantation into a mammalian organism. The method involves placing the drug-loaded device interface window in contact with the targeted tissue. The method includes sealing the device to the target tissue by way of adhesives, buckling or suturing or the combination of any of those. To build the adhesive layer it preferentially uses but is not limited to a hydrogel, hyaluronate and fibrin adhesive. It is incorporated to the sealing base by the use of a film or layer containing adhesive in its both sides, or by the pre-application of the adhesive to the internal side of the sealing base. For holding the adhesive in place multiple cavities, single cavity or a channel system along the internal surface of the sealing base are preferentially used. Such sealing structures are made preferentially during the molding process of the device. After placement of the adhesive in contact to the base, a film may be placed in contact to the adhesive layer. Preferentially the film is non-reactive with the adhesive used and can peeled off before the implantation procedure. The use of an exposed sealing base, presenting the structures mentioned above to hold the adhesive in place allows also its application right before the implantation procedure, particularly if a biological adhesive such as fibrin sealant is desired to be used.

The device may be interfaced with an artificial organ, a synthetic or biological platform for cells or biological agents, a scaffold for tissue or cell regeneration, and/or a transplanted tissue or organ.

The method of the present invention can achieve local or systemic, physiological or pharmacological effects in a mammalian organism, by using a surgically implantable device that delivers an agent directly and preferentially through its interface with the targeted tissue or organ, keeping the rest of its surface non-permeable to the carried agent.

The therapeutic agent may be a prophylactic agent. The system or device may carry an osmotic agent.

The effect or diffusion of the agent may be started or enhanced after the implantation procedure through the use of a secondary agent, whether it is chemical, physical or biological.

Some non-limiting examples of diseases for which the present inventions may be used include, myocardial ischemic disease, hepatic cancers, hepatic metastasis of colon cancers, gall bladder tumors, adrenal tumors, neuroblastomas, and kidney and pancreatic cancers. The device of the present invention can be loaded with the desired active agent (i.e., drug(s) and/or prodrug(s)) and can be implanted and attached to an anatomical or histological surface. For example, the device can be glued to the pericardium surface to deliver an agent to the pericardial space, allowing the drug in the reservoir to diffuse to the whole myocardium. It can also, through an opening of the pericardium, be glued directly to the myocardium (note that the pericardium is a sac, mostly acellular, but is delineated from other structures by a histopathological and anatomical surface, and the myocardium which is mostly cellular, is also delineated by the pericardium by surface, which is ultimately the muscle cell, but there is still a distinguished surface). It is preferred that the device not be implanted inside the myocardium to deliver drug to a deeper layer of the muscle or a specific group of cells, as it is preferred that such invasive techniques be minimized. Hence, it is preferred that the devices, when implanted, not degrade the histological structure of the tissue that will be treated (the target).

In an embodiment, the present invention has numerous applications in ophthalmology, with the eye providing several locations where loaded devices may be applied. Preferentially, in Ophthalmology, the device is used to be in placed in contact to the sclera. Alternatively, between the outer layer of the eye, known as the sclera, and the vitreous there is suprachoroidal space (accessible through a scleral incision) or even the subretinal space. For the subretinal space, either a choroidal incision or a retinotomy could be made to allow the insertion of the implant. Diseases in ophthalmology that may be treated with the present inventions and other ophthalmic applications of the present invention include but are not limited to intraocular tumors, e.g. retinoblastoma, melanoma, macular degeneration, delivery to the posterior pole (e.g., choroidal and RPE layers) of growth factors, antiangiogenic factors, photosensitizers (which may be subject to application of laser), gene vectors, etc. The present invention may be applied to glaucoma by delivering antiglaucoma drug(s) via the device to the cilliary body directly through the sclera. The present invention may also be applied to retinitis pigmentosa, to deliver growth factors or to deliver immunosupressive agents to protect a retina or RPE graft, without an intraocular surgical procedure that would jeopardize the graft.

The present invention is designed for implantation, rather than for external body surface or buccal applications. The present invention makes possible the targeting of specific tissues within the body or eye, and takes into account that many drugs are more specific and toxic to certain groups of cells than others. In situations where the surrounding target tissue can be harmed by the applied drug, the present invention provides a superior solution by focusing the drug on the target tissue.

In addition to treating localized diseases, the present invention can be used to provide systemic benefits. Using a system of the present invention to deliver growth factors to the pancreas of a diabetic patient can change the context of the systemic disease. Application of appropriate agents using the system of the present invention to an inoperable liver affected by a colonic metastatic carcinoma can reduce the size of the tumor and make it ressectable. In addition to cures, the present invention can also be used for treatments aimed to improve the quality of life of patients, or improve their cost-effectiveness. The local delivery of cytotoxic agents by the device to a tumor expanding and compressing the esophagus can make a difference in the patient's quality of life preventing more complex interventions, such as a surgical ressection. Thus, even palliative care is facilitated by the present invention. The invention is particularly useful in tumor treatments when the tumor or effected organ has a distinguishable surface to which can be sealed the interface window incorporated in a drug delivery device of the present invention.

The method of delivering the loaded drug delivery devices of the present invention may involve a variety of implantation techniques either manually or through an injector. The devices may be implanted under direct visualization or under indirect visualization techniques, such as ultrasound, MRI, CT-scan guided, laparoscopy, etc.

While exemplary embodiments of the present invention have been set forth above, it is to be understood that the pioneer inventions disclosed herein may be constructed or used otherwise than as specifically described.

The invention claimed is:

1. An implantable delivery device for delivery of at least a first therapeutic agent into a target tissue, comprising:
   a housing, said housing comprising a reservoir with a release port for release of at least a first therapeutic agent into a target tissue, said reservoir having at least a first wall that is substantially impermeable to a first therapeutic agent to be placed therein,
   a sealing base for sealing said release port to a target tissue, wherein when said release port is sealed to a target tissue a first therapeutic agent in said reservoir is substantially prohibited from release by said device other than through said release port into the target tissue, and
   an attachment mechanism to facilitate sealing of said release port to a target tissue, said attachment mechanism comprising at least one member of the group consisting of a sufficient amount of an adhesive for adhering said sealing base to a target tissue wherein said adhesive is held within at least one cavity or channel within said sealing base, and at least one stabilizer on said first wall for engaging a buckling band or suture for sealably engaging said device with a target tissue.

2. The device of claim 1, wherein said target tissue is eye tissue.

3. The device of claim 1, wherein said release port has a perimeter, and said sealing base surrounds at least a portion of said perimeter, wherein said sealing base can be engaged by at least one suture to fix said device to a target tissue so that said release port is sealed to the tissue.

4. The device of claim 1, wherein said stabilizer comprises a suture holder, said release port has a perimeter, and said suture holder comprises at least one structure on said first wall, said structure selected from the group consisting of a bump on said first wall, and a depression in said first wall, wherein said at least one structure can be engaged by at least one suture to fix said device to a target tissue so that said release port is sealed to the tissue.

5. The device of claim 1, wherein said at least a first wall forming said reservoir comprises at least one material selected from the group consisting of an elastic material and a flexible material.

6. The device of claim 1, wherein said at least a first wall comprises at least one material selected from the group consisting of polyethylene, a silicone polymer, a hydrogel, a polyglycolic acid, a polylactic acid, a polycaprolactone, a polyvinyl alcohol, a polyorthoester, and a polyvinylpyrrolidone.

7. The device of claim 1, wherein said at least a first wall comprises at least one material selected from the group consisting of polyethylene, and a silicone polymer.

8. The device of claim 1, wherein said device further comprises a refill port.

9. The device of claim 8, wherein said refill port is visually distinguishable from said at least first wall.

10. The device of claim 8, wherein said refill port is formed of a self sealing polymer.

11. The device of claim 8, wherein said refill port projects outward from said device to facilitate access.

12. The device of claim 1, further comprising a first therapeutic or prophylactic agent.

13. The device of claim 12, wherein said first agent is selected from the group consisting of an antineoplastic agent, a peptide, an antibody, gene vector, hormone, protein, a radiosensitizer, a photosensitizer, a chemosensitizer, mammalian cells, a virus, a bacteria, and a nucleotide.

14. The device of claim 1, further comprising a cytotoxic agent.

15. The device of claim 12, further comprising a vehicle for said agent.

16. The device of claim 15, wherein said vehicle comprises at least one material selected from the group consisting of a poly-orthoester, a poly-glycolic acid, a poly-lactic acid, a poly-caprolactone, an acrylate, a cellulose, a poly-vinyl-alcohol, polyvinylpyrrolidone, dextran, hyaluronic acid, fibrin, collagen, and gelatin.

17. The device of claim 15, wherein the state of said vehicle is selected from the group consisting of solid, liquid, and gel, and the state of said agent is selected from the group consisting of solid, liquid and gel.

18. The device of claim 13, further comprising at least one therapeutic enhancer agent selected from the group consisting of an enzyme, a co-drug, and a substract of said therapeutic agent.

19. The device of claim 13, further comprising at least one therapeutic enhancer agent, said therapeutic enhancer agent comprising a protein.

20. The device of claim 19, wherein said protein comprises albumin.

21. The device of claim 13, further comprising a perfusion enhancer, said perfusion enhancer being capable of enhancing the penetration of said therapeutic or prophylactic agent into a target tissue.

22. The device of claim 21, wherein said perfusion enhancer comprises at least one compound selected from the group consisting of comprises an enzyme, a pro-enzyme, and a prostaglandin.

23. The device of claim 22, wherein said enzyme comprises at least one enzyme selected from the group consisting of collagenases, and a matrix metalloproteinase.

24. The device of claim 1, further comprising a barrier layer covering said release port.

25. The device of claim 24, wherein said barrier layer comprises a material selected from the group consisting of gelatin; hyaluronic acid, methyl cellulose, polyglycolic acid, and polylactic acid.

26. The device of claim 5, wherein said device is sufficiently flexible to allow insertion through an incision smaller in dimensions than the largest dimension of said device and allows sealable attachment to an irregular organ surface.

27. The device of claim 1, wherein said attachment mechanism comprises at least one stabilizer on said first wall for engaging a buckling band or suture for sealably engaging said device with a target tissue.

28. The device of claim 1, further comprising a buckling band, wherein said buckling band can encircle said device and a portion of an organ to which said device is attachable.

29. The device of claim 28, wherein said buckling band can engage said device with the sclera of an eye.

30. The device of claim 1, wherein said stabilizer is shaped to engage a buckling band for secure attachment of said device to a surface, said surface being the sclera of an eye.

31. The device of claim 12, wherein said agent is in an encapsulated form.

32. The device of claim 12, wherein said agent is incorporated into liposomes or microspheres.

33. The device of claim 12, wherein said agent is in an inactive form.

34. The device of claim 15, wherein said vehicle comprises at least one of the group consisting of a polymer, a copolymer, and a tissue.

35. The device of claim 15, wherein said vehicle interacts with said agent to control release thereof.

36. The device of claim 12, further comprising a substance for controlling the release of said agent.

37. The device of claim 1, wherein said reservoir comprises at least two compartments.

38. The device of claim 37, wherein said at least two compartments are divided by a wall that also divides said release port into at least two outlets corresponding to each of said at least two compartments, at least a portion of said wall is capable of sealable attachment to a tissue when said sealing base is attached thereto, wherein agents contained in separate compartments of said at least two compartments are substantially isolated from each other.

39. The device of claim 12, further comprising a second therapeutic or prophylactic agent, wherein said second therapeutic agent can be delivered to a target tissue after a portion of said first therapeutic or prophylactic agent is delivered to a target tissue.

40. The device of claim 12, further comprising an osmotic agent.

41. The device of claim 24, wherein said barrier layer is biodegradable.

42. A method of targeted delivery of a therapeutic or prophylactic substance to a tissue, comprising delivering a therapeutic or prophylactic substance to a target area of a tissue using the device of claim 1.

43. The method of claim 42, wherein said target area comprises myocardial tissue.

44. The method of claim 42, wherein said target area comprises scleral tissue.

45. The method of claim 42, wherein said target area comprises pericardial tissue.

46. The method of claim 42, wherein said target area comprises hepatic tissue.

47. The method of claim 42, wherein said target area comprises renal tissue.

48. The method of claim 42, wherein said target area comprises uterine tissue.

49. The method of claim 42, wherein said substance is delivered to treat cancer.

50. The method of claim 42, wherein said substance is delivered to treat retinoblastoma.

51. The method of claim 42, wherein said substance is delivered to cause an effect selected from the group consisting of treatment of an ocular disorder, treatment of a renal disorder, treatment of a hepatic disorder, treatment of a cardiac disorder, treatment of a gastrointestinal disorder, treatment of a genital-urinary disorder, treatment of an endocrine disorder, treatment of a neurological disorder, and treatment of an immunological disorder.

52. The method of claim 51, wherein said treatment is prophylactic.

53. The method of claim 51, wherein said ocular disorder is selected from the group consisting of an ocular tumor, glaucoma, a macular degenerative condition, and an immune response to an ocular surgery.

54. The method of claim 42, wherein the substance is delivered to a target tissue to cause an effect other than or in addition to an effect caused in said target tissue.

55. The method of claim 42, wherein the target tissue is transplanted tissue.

56. The method of claim 42, wherein said tissue comprises a material selected from the group consisting of mammalian tissue, an artificial organ, and a synthetic or biological scaffold for cells or biological agents.

57. The method of claim 42, wherein said tissue is transplant tissue.

58. The device of claim 1, wherein said device further comprises at least one first therapeutic agent, wherein the effect or diffusion of said at least one first therapeutic agent may be started or enhanced by the use of at least one second agent selected from the group consisting of a biological agent, a physical agent, and a chemical agent.

59. The device of claim 1, wherein said sealing base has a similar curvature as the targeted tissue surface.

60. The device of claim 1, wherein said sealing base comprises at least one cavity to hold an adhesive in place.

61. The device of claim 1, wherein said sealing base comprises at least one channel to hold an adhesive in place.

62. The device of claim 1, wherein said sealing base is composed of a different material from said first wall.

63. The device of claim 62, wherein said sealing base is composed of a material selected from the group consisting of a poly-ethylene, silicone, a hydrogel, a poly-orthoester, poly-glycolic acid, poly-lactic acid, poly-caprolactone, polyvinyl-alcohol, polyvinyl-pylirridone, hyaluronic acid, fibrin, methyl-cellulose, collagen, and gelatin.

64. The device of claim 37, further comprising at least one refill port connected to said reservoir.

65. The device of claim 1, wherein said release port has a perimeter, and said sealing base surrounds said release port perimeter.

66. An implantable delivery device for delivery of at least a first therapeutic agent into a target tissue, comprising:
a housing, said housing comprising a reservoir with a release part for release of at least a first therapeutic agent into a target tissue, said reservoir having at least a first wall that is substantially impermeable to a first therapeutic agent to be placed therein, a sealing base for sealing said release port to a target tissue, wherein when said release port is sealed to a target tissue a first therapeutic agent in said reservoir is substantially prohibited from release by said device other than through said release port into the target tissue, and
an attachment mechanism to facilitate sealing of said release port to a target tissue,
wherein said attachment mechanism comprises a sufficient amount of an adhesive for adhering said sealing base to a target tissue, wherein said adhesive is held within at least one cavity or channel within said sealing base.

67. The device of claim 66, wherein said adhesive comprises at least one of the group consisting of fibrin, hydrogel, and hyaluronate.

68. The device of claim 66, wherein said adhesive comprises an acrylate.

69. The device of claim 66, further comprising a peelable layer apposed to said adhesive.

70. An implantable delivery device for delivery of at least a first therapeutic agent into a target tissue, comprising:
a housing, said housing comprising a reservoir with a release port for release of at least a first therapeutic agent into a target tissue, said reservoir having at least a first wall, a sealing base for sealing said release port to a target tissue, wherein when said release port is sealed to a target tissue a first therapeutic agent in said reservoir can be released through said release port into the target tissue, and
an attachment mechanism to facilitate sealing of said release port to a target tissue, wherein said attachment mechanism comprises a suture holder for engaging at least one suture operatively attached to tissue surrounding a target tissue, and wherein said first wall is impermeable to a first therapeutic agent placed in said reservoir, wherein said release port has a perimeter, and said suture holder comprises at least one groove in said first wall, wherein said at least one groove can be engaged by at least one suture or buckling band to fix said device to a target tissue so that said release port is sealed to the tissue.

71. An implantable delivery device for delivery of at least a first therapeutic agent into a target tissue, comprising:
a housing, said housing comprising a reservoir with a release port for release of at least a first therapeutic agent into a target tissue, said reservoir having at least a first wall, a sealing base for sealing said release port to a target tissue, wherein when said release port is sealed to a target tissue a first therapeutic agent in said reservoir can be released through said release port into the target tissue, and
an attachment mechanism to facilitate sealing of said release port to a target tissue,
wherein said device further comprises a refill port, wherein said refill port comprises a material selected from the group consisting of a dye, a radiosensitive marker, and an echogenic marker so that said refill port is indicated by said material.

72. An implantable delivery device for delivery of at least a first therapeutic agent into a target tissue, comprising:
a housing, said housing comprising a reservoir with a release port for release of at least a first therapeutic agent into a target tissue, said reservoir having at least a first wall that is substantially impermeable to a first therapeutic agent to be placed therein,
a sealing base for sealing said release port to a target tissue, wherein when said release port is sealed to a target tissue a first therapeutic agent in said reservoir is substantially prohibited from release by said device other than through said release port into the target tissue, and
an attachment mechanism to facilitate sealing of said release port to a target tissue, said attachment mechanism comprising at least one member of the group consisting of a sufficient amount of an adhesive for adhering said sealing base to a target tissue wherein said adhesive is held within at least one cavity or channel within said sealing base, and at least one stabilizer on said first wall for engaging a buckling band or suture for sealably engaging said device with a target tissue, wherein said sealing base has a greater curvature than the targeted tissue surface.

* * * * *